US00PP10983P

United States Patent [19]

Guillou et al.

[11] Patent Number: Plant 10,983

[45] Date of Patent: Jun. 29, 1999

[54] GERANIUM PLANT NAMED 'GUIFLAM'

[75] Inventors: Bernard Guillou; Jacques Guillou; Maurice Guillou, all of Saint-Malo, France

[73] Assignee: Guillou Freres J.B. ET M., St. Malo, France

[21] Appl. No.: 08/724,504

[22] Filed: Sep. 30, 1996

[51] Int. Cl.[6] ..... A01H 5/00

[52] U.S. Cl. ..... Plt./332

[58] Field of Search ..... Plt./87.12, 332

[56] References Cited

U.S. PATENT DOCUMENTS

P.P. 8,551 1/1851 Klemm ..... Plt./87.12

P.P. 9,237 8/1952 Klemm ..... Plt./87.12

OTHER PUBLICATIONS

UPOV CD Rom, PBR PEL 00371, Germany, 'Kleflam' Pelargonium, 1990.

*Primary Examiner*—Howard J. Locker
*Assistant Examiner*—Melissa L. Kimball
*Attorney, Agent, or Firm*—Foley & Lardner

[57] ABSTRACT

A new geranium plant named 'Guiflam', characterized by double-type flowers with 11–15 petals per flower that are intensely red in color; corolla diameter of approximately 60 mm; early to semi-early flowering which is luxuriant in the summer; branch internode length of approximately 30 to 50 mm, plant height of approximately 30 cm, and ivy-shaped foliage that is dentated and veined.

3 Drawing Sheets

The present invention comprises a new and distinct cultivar of geranium, botanically known as *Pelargonium peltatum* l'Hér. ex Ait, and hereinafter referrred to by the cultivar name 'Guiflam'. 'Guiflam' is a product of planned breeding program which had the objective of creating new geranium cultivars with a red flower color and compact and well-branched plant habit.

'Guiflam' was originated from a hybridization made in a controlled breeding program in Saint Malo, Bretagne, France in 1988. The male and female parents were 'Corot' (unpatented cultivar), and 'Tavira', respectively. 'Tavira' is from the proprietary Guillou collection. Both parents are characterized by flowers with an intense red color and double-type structure.

'Guiflam' was discovered and selected as one flowering plant within the progeny of the stated cross by the inventors in 1991 in a controlled environment in Saint Malo, France.

The first act of asexual reproduction, of 'Guiflam' was accomplished when vegetative cuttings were taken from the initial selection in 1994 in a controlled environment in Haalderen, The Netherlands, by a technician working under the supervision of the inventors. Horticultural examination of selected units initiated in 1994 has demonstrated that the combination of characteristics as herein disclosed for 'Guiflam' are firmly fixed and are retained through successive generations of asexual reproduction.

'Guiflam' has not been observed under all possible environmental conditions. The phenotype may vary with variations in environment such as temperature, light intensity, and day length, without any change in genotype. The following observations, measurements, and comparisons describe plants grown in Haalderen, The Netherlands, under greenhouse conditions which approximate those generally used in commercial practice.

The following traits have been repeatedly observed to be basic characteristics of 'Guiflam' which in combination distinguish this geranium as a new and distinct cultivar:

1. Intensely red double-type flowers.
2. Deep green downy foliage with dentate edges.
3. Early/semi-early flowering which is very luxuriant in summer.
4. Regular flowers displayed on attractive foliage.

Of the many commercial cultivars known to the present inventors, 'Guiflam' most closely resembles 'Corot' and 'Tavira' in plant habit.

The accompanying photographic drawings show typical flower and foliage characteristics of 'Guiflam'.

Sheet 1 is a side view of the plant showing flowers at various stages of maturity.

Sheet 2 is a top and bottom view of an individual flower.

Sheet 3 is a top and bottom view of an individual leaf of 'Guiflam'.

In the following description, color references are made to The Royal Horticultural Society (R.H.S.) Colour Chart. The color values were determined indoors in 1996 under greenhouse conditions at Haalderen, The Netherlands. Colors are as true as possible with illustrations of this type.

Classification:

*Botanical.*—*Pelargonium peltatum* l'Hér. ex Ait. cv. 'Guiflam'.

*Commercial.*—Ivy geranium.

INFLORESCENCE

A. Umbel:

*Average diameter.*—70–90 mm.

*Average depth.*—35 mm.

*Pedicel length.*—80 mm in greenhouse.

B. Corolla:

*Average diameter.*—60 mm.

*Form.*—Double-type.

*Number of petals.*—11–15.

*Color* (*generally tonality from a distance of three meters*).—Intense red.

*Color* (*abaxial*).—Approx. R.H.S. 46B.

*Color* (*adaxial*).—Approx. R.H.S. 46C.

C. Bud:

*Size.*—12 mm.

*Color* (*abaxial*).—Approx. R.H.S. 44B.

*Color* (*adaxial*).—Approx. R.H.S. 44B.

D. Reproductive organs.

*Androecium.*—Copious pollen.

*Gynoecium.*—Strongly developed.

E. Spring flowering response period: 6–8 flowers opened 15 weeks after planting of unrooted cuttings (pinched plants).
F. Outdoor flower production: Abundant flower production in summer.
G. Durability: Shatter resistance medium.

PLANT

A. Foliage:
*Form.*—Ivy-shaped.
*Margin.*—Dentated and veined; diameter (5 round lobes of 80 mm diam.).
*Color* (*abaxial*).—Deep green approx. R.H.S. 146A
*Color* (*adaxial*).—Deep green, approx. R.H.S. 146A
B. General appearance and form:
*Internode length.*—30–50 mm.
*Branching pattern.*—4–5 branches/plant.
*Height.*—30 cm.
C. Tolerance to botrytis: Good resistance.

We claim:

1. A new and distinct cultivar of geranium plant named 'Guiflam', as illustrated and described.

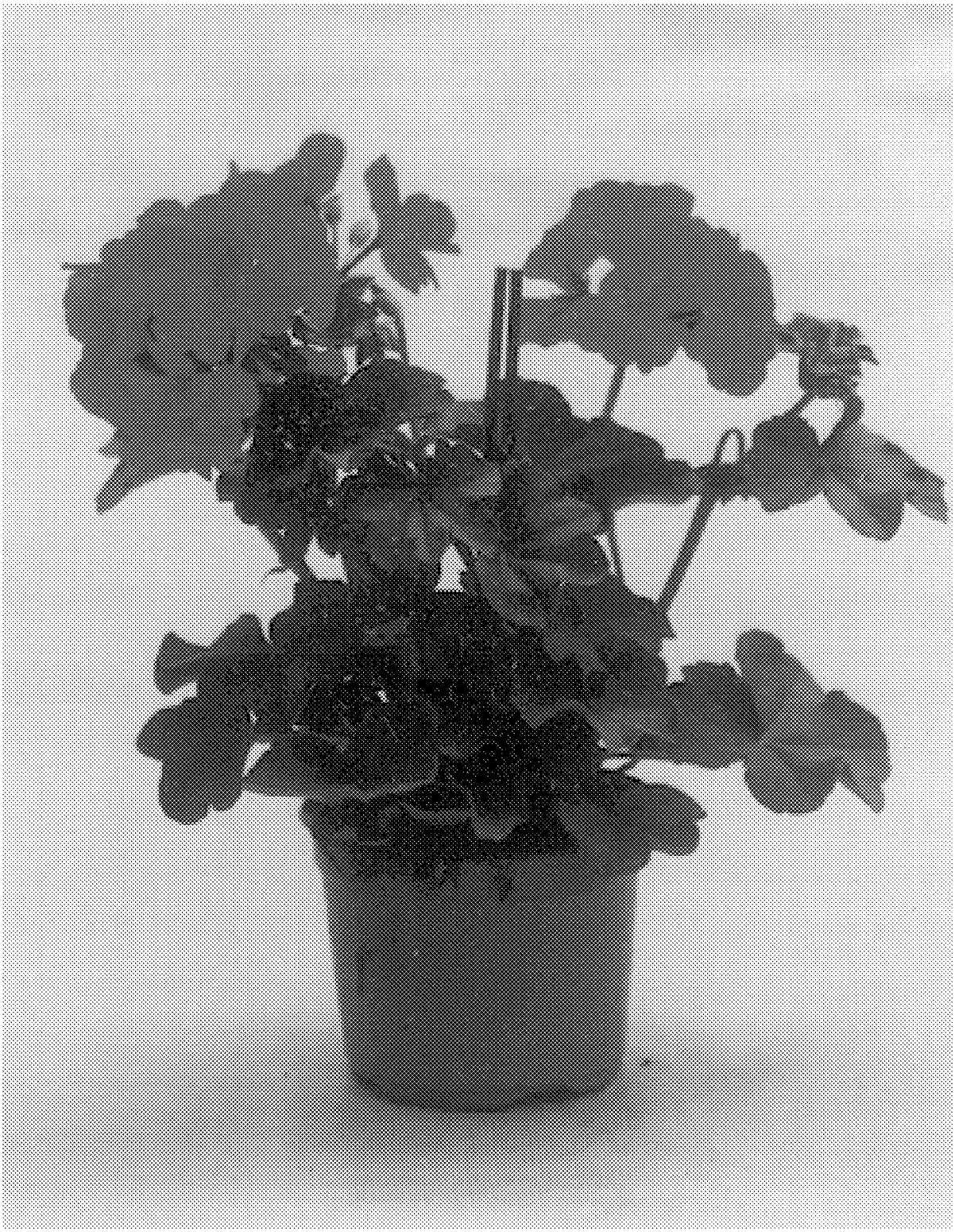

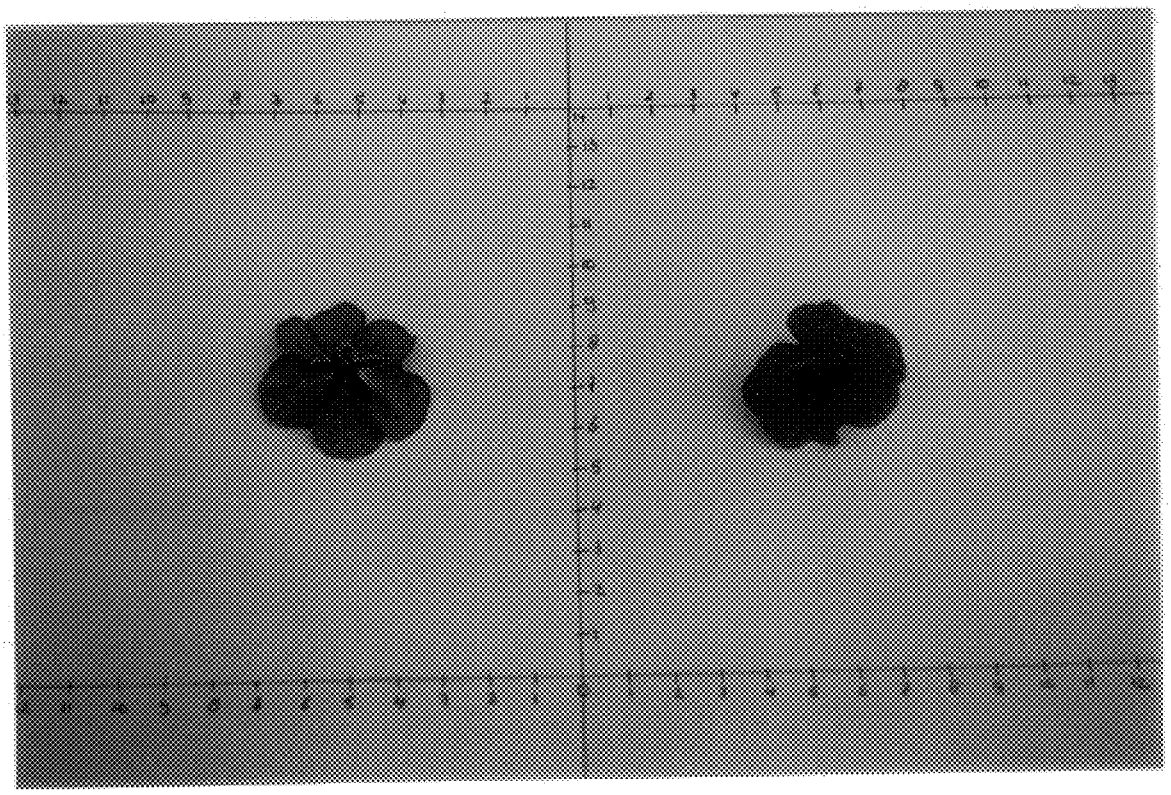

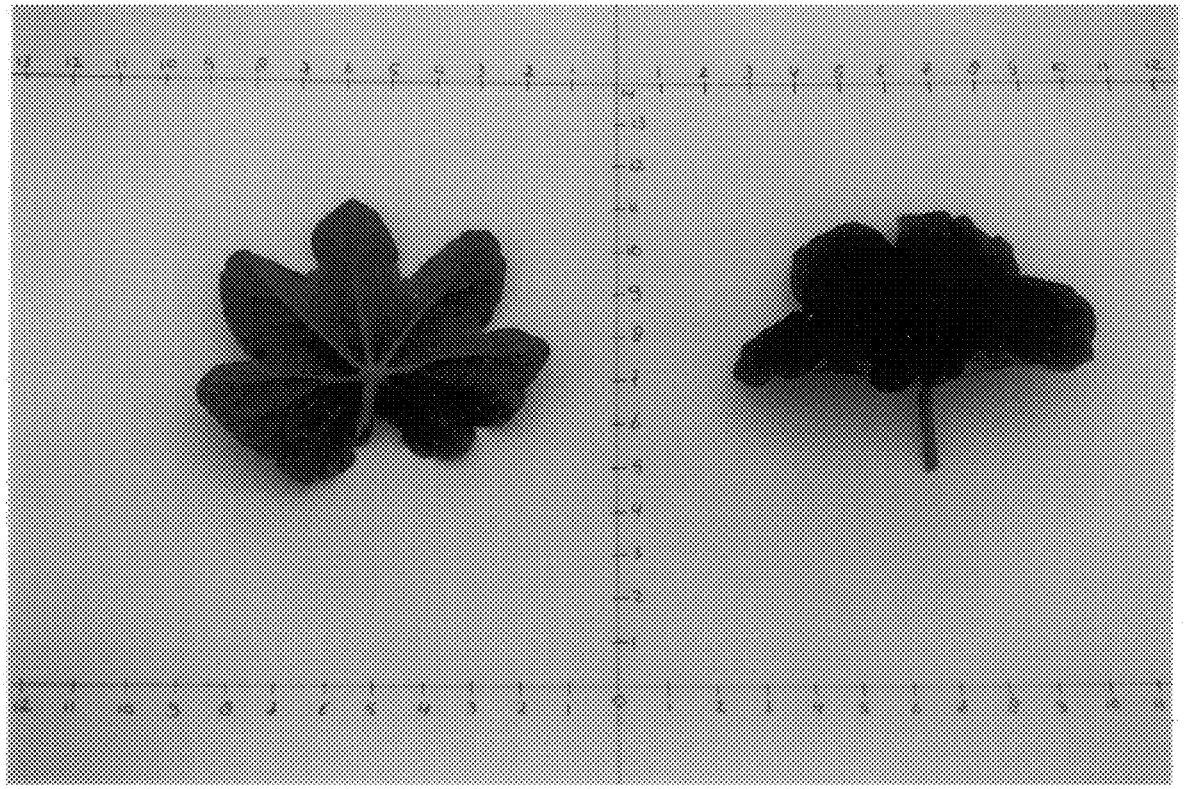

* * * * *